US011660600B2

(12) United States Patent
Lin et al.

(10) Patent No.: US 11,660,600 B2
(45) Date of Patent: May 30, 2023

(54) MICROFLUIDIC DEVICE WITH RESERVOIR INTERFACE

(71) Applicant: The Johns Hopkins University, Baltimore, MD (US)

(72) Inventors: Jeffrey S. Lin, Silver Spring, MD (US); Andrew B. Feldman, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 139 days.

(21) Appl. No.: 17/387,566

(22) Filed: Jul. 28, 2021

(65) Prior Publication Data

US 2023/0034468 A1 Feb. 2, 2023

(51) Int. Cl.

| | |
|---|---|
| ***C12N 15/10*** | (2006.01) |
| ***B01L 3/00*** | (2006.01) |
| ***B01L 7/00*** | (2006.01) |
| ***F28F 3/12*** | (2006.01) |

(52) U.S. Cl.

CPC ..... *B01L 3/50273* (2013.01); *B01L 3/502715* (2013.01); *B01L 2200/027* (2013.01); *B01L 2200/0605* (2013.01); *B01L 2400/049* (2013.01); *B01L 2400/0487* (2013.01)

(58) Field of Classification Search

CPC ........... B01L 3/50273; B01L 3/502715; B01L 2200/027; B01L 2200/0605; B01L 2400/0487; B01L 2400/049

See application file for complete search history.

(56) References Cited

FOREIGN PATENT DOCUMENTS

WO WO-2022038376 A1 * 2/2022

* cited by examiner

*Primary Examiner* — Jennifer Wecker
*Assistant Examiner* — Oyeleye Alexander Alabi
(74) *Attorney, Agent, or Firm* — Todd R. Farnsworth

(57) ABSTRACT

A microfluidic assembly may include a microfluidic chip operably coupled to a device source pressure port and a device relief pressure port, first and second input reservoirs, an output reservoir, and a reservoir interface. The microfluidic chip may include a microfluidic circuit configured to support a fluid flow that includes a gas flow and a liquid flow within the microfluidic circuit. The reservoir interface may be configured to operably couple the first and second input reservoirs to the microfluidic circuit. The device source pressure port may be configured to receive a source pressure to generate the fluid flow through the microfluidic circuit and cause a mixing of liquids to form an output liquid for delivery to the output reservoir via the fluid flow. The first liquid, the second liquid, and the output liquid need not contact the device source pressure port or the device relief pressure port during the mixing.

20 Claims, 10 Drawing Sheets

MICROFLUIDIC DEVICE WITH RESERVOIR INTERFACE

TECHNICAL FIELD

Example embodiments generally relate to microfluid technology and, in particular, relate to a microfluidic device including an improved reservoir interface.

BACKGROUND

Microfluidic technologies are used in many scientific, laboratory, and industrial applications. In particular, devices that leverage the operation of microfluidic channels have proven to be very useful for imaging and mixing substances in a variety of fields including cell biology, genetics, fluid dynamics, tissue engineering, fertility testing, synthesis of chemicals and proteins, and the like. Such devices leverage the principles of microfluidics, which involves the study of fluids in amounts smaller than a droplet. To form such small amounts, many devices use microfluidic channels that have a width that is submicron to a few millimeters. These microfluidic channels may be formed in a device that is referred to as a microfluidic chip. The microfluidic channels of the chip permit processing (e.g., mixing, chemical reactions, physical reactions, or the like), as well as, visualization and imaging of such processing. The fluid or fluids applied to the microfluidic chip may include any type of particles including biologic material, such as proteins and other types of cells, chemicals, or the like.

However, despite their high utility in a number of contexts, many microfluidic systems can be cumbersome to maintain and operate particularly when applications demand high processing throughput rates. In such applications, issues relating to, for example, cross-contamination between processing operations must be avoided. For example, in medical diagnostics and biomolecular forensics, cross-contamination can lead to inaccurate results and serious ramifications due to false positives. In these cases, any residual fluids from previous processing can generate such false results and invalidate the utility of the later processing. As such, any material or devices that come into contact with the fluids of a particular processing run must either be discarded or thoroughly cleaned. This required cleaning process often involves taking the microfluidic system offline so that components of the system can be removed, cleaned, and verified as having been sufficiently cleaned. In particular, tubing, manifold components, and the like can require such cumbersome cleaning efforts or disposal resulting in high system downtimes and added cost of operation. As such, it would be beneficial to develop microfluidic devices that can minimize or eliminate the post-process cleaning and one-time use peripheral components.

BRIEF SUMMARY OF SOME EXAMPLES

According to some example embodiments, a microfluidic assembly is provided. The microfluidic assembly may comprise a device source pressure port, a device relief pressure port, a microfluidic chip operably coupled to the device source pressure port and the device relief pressure port, a first input reservoir and a second input reservoir, an output reservoir, and a reservoir interface. The microfluidic chip may comprise a microfluidic circuit configured to support a fluid flow through the microfluidic circuit. The fluid flow may comprise a gas flow and a liquid flow within the microfluidic circuit. The reservoir interface may be configured to operably couple the first input reservoir and the second input reservoir to the microfluidic circuit. The device source pressure port may be configured to receive a source pressure to generate a fluid flow between the device relief pressure port and the device source pressure port and through the microfluidic circuit. The fluid flow may cause a mixing of a first liquid in the first input reservoir with a second liquid in the second input reservoir at a mixing junction of the microfluidic circuit within the microfluidic chip to form an output liquid for delivery to the output reservoir via the fluid flow. The first liquid, the second liquid, and the output liquid need not contact the device source pressure port or the device relief pressure port during the mixing.

According to some example embodiments, a microfluidic reservoir interface is provided. The microfluidic reservoir interface may comprise a liquid pipe configured to extend into a liquid within a reservoir, a gas interface, and an interface base configured to support the liquid pipe and the gas interface. The liquid pipe may be configured to be operable coupled to a liquid channel portion of a microfluidic circuit of a microfluidic chip and the gas interface may be configured to be operably coupled to a gas channel portion of a microfluidic device. The liquid pipe may be configured to transport the liquid between the reservoir and the liquid channel portion in response to a fluid flow through the liquid pipe and the gas interface.

According to some example embodiments, a method for performing a mixing of liquids is provided. The method may comprise receiving a source pressure applied at a device source pressure port of a microfluidic device, generating a pressure differential and a fluid flow between a device relief pressure port and the device source pressure port through the microfluidic circuit due to receiving the source pressure, and transporting a first liquid from a first input reservoir into the microfluidic circuit due to the fluid flow through the microfluidic circuit. The method may further comprise transporting a second liquid from a second input reservoir into the microfluidic circuit due to the fluid flow through the microfluidic circuit, causing a mixing of the first liquid with the second liquid at a mixing junction of the microfluidic circuit to form an output liquid, and transporting the output liquid to an output reservoir due to the fluid flow through the microfluidic circuit. The first liquid, the second liquid, and the output liquid need not contact the device source pressure port or the device relief pressure port during the mixing.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

DETAILED DESCRIPTION

Figure 1A:
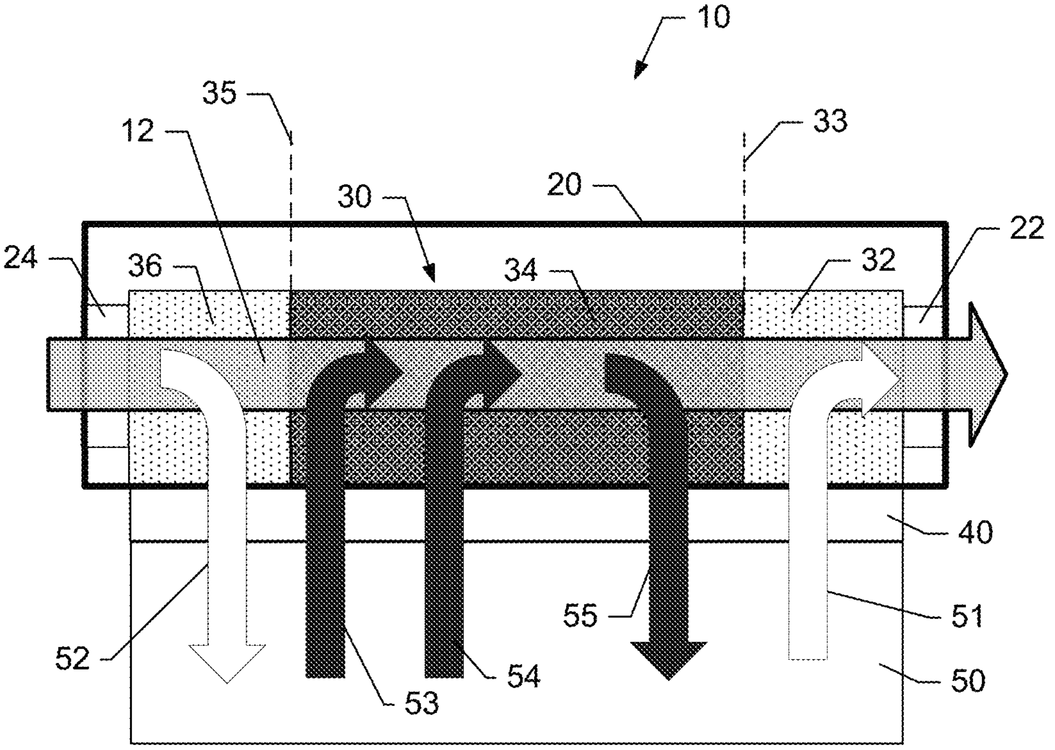
FIG. 1A illustrates an example microfluidic device and a fluid flow through the microfluidic device according to some example embodiments.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

According to some example embodiments, a microfluidic device is described that comprises a microfluidic chip and a reservoir interface configured to operably couple input and output reservoirs to the microfluidic chip. The microfluidic device may operate to create microfluidic mixtures from input fluids, where the fluid flow within the device that operates to form the mixture is controlled by application of external gas pressures thereby avoiding liquid contact interactions with any components external to the microfluidic device. Such external gas pressures (e.g., positive or negative pressures) may be applied at the device source pressure port, in controlled manner, to generate a pressure differential and an associated fluid flow between the device source pressure port and a device relief pressure port. Based on whether the applied source provides a positive pressure or a negative pressure, the source may be applied, relative to the direction of the fluid flow, in an upstream position for a positive pressure source or a downstream position for a negative pressure source. As such, a given port of the microfluidic device may be defined as a device source pressure port or device relief pressure port based upon whether the source is a positive pressure source or a negative pressure source. In either case, an example microfluidic device may have a device pressure source port and a device pressure relief port that form the external interfaces to an external processing control system. These ports may operate as gas pressure interfaces that do not come into contact with any liquids that are involved in the microfluidic processing.

Additionally, these gas pressure interfaces can operate to force the liquids into a microfluidic circuit that is disposed, at least partially, within a microfluidic chip to perform an operation, such as a mixing operation. The microfluidic chip, according to some example embodiments, may be a transparent block of material with internal microfluidic channels and a mixing junction of the microfluidic circuit for transporting, combining, and manipulating liquids, where the channels are tens to hundreds of microns in diameter. Accordingly, a fluid flow (i.e., a gas and/or liquid flow) through the microfluidic chip can be formed within the microfluidic circuit without the fluid flow causing liquid contact with components external to the microfluidic device. As such, according to some example embodiments, after a microfluid mixture is formed using the microfluidic device, only the device itself is contaminated by the mixing process and therefore the microfluidic device may simply be replaced within an external mixture control system to conduct a subsequent mixture process, without having to clean or replace interface tubing, interface manifolds, or other interface components to an external processing control system. Additionally, once the results of a mixture process are removed from the reservoirs, microfluidic device and the reservoirs may be disposed. However, according to some example embodiments, the microfluidic device may be cleaned and reused in, for example, a separate, offline process that does not affect throughput at processing control stations.

As such, a microfluidic assembly, according to some example embodiments, may comprise a microfluidic device and an external processing control system. The microfluidic device, according to some example embodiments, may comprise a microfluidic chip having a microfluidic circuit, a reservoir interface configured to operate as an operational interface between the microfluidic chip and one or more reservoirs from which an input liquid may be extracted or an output liquid may be delivered, and a processing control interface which may comprise the device source pressure port and the device relief pressure port. The microfluidic circuit of the microfluidic chip may be operably coupled to reservoirs via the reservoir interface and the microfluidic device may be operably coupled to a processing control system via at least the device source pressure port, and also, possibly the device relief pressure port. The reservoir interface may therefore support liquid and gas flows into and out of the reservoirs to support the fluid flow through the microfluidic circuit.

Further, according to some example embodiments, the microfluidic device may comprise a source pressure gas portion operably coupled to the device source pressure port and a relief pressure gas portion operably coupled to the device relief pressure port. A liquid channel portion of the microfluidic chip may be disposed between the source pressure gas portion and the relief pressure gas portion. These gas portions may operate as contaminant barriers to the liquid channel portion with respect to external components of, for example, the processing control system. Moreover, the source pressure gas portion and the relief pressure gas portion may operate as contamination barriers that bracket the liquid channel portion because, according to some example embodiments, only liquid flows in the liquid channel portion of the microfluidic circuit and only non-contaminant gases (e.g., air) flow in the source pressure gas portion and the relief pressure gas portion. In this manner, according to some example embodiments, cross-contamination between microfluidic processing runs can be avoided without requiring cleaning and/or disposal of some or all components external to the microfluidic device.

Now referring to FIG. 1A, example microfluidic device 10 is shown in combination with reservoirs 50. The description of the microfluidic device 10 is provided in the context of a vacuum or negative source, such that the source components and elements are located in downstream positions and the relief components and elements are in upstream positions relative to the fluid flow 12. However, one of ordinary skill in the art would appreciate that the references to source and relief components and elements may simply be exchanged in the context of a positive pressure source that would be placed in an upstream position relative to the fluid flow 12.

The microfluidic device 10 may comprise a microfluidic chip 20 and a reservoir interface 40. The microfluidic chip 20 may be constructed from a solid substance formed as, for example a block, and may be transparent or sufficiently translucent to allow for visualization and imaging of the operations performed within the microfluidic chip 20. In this regard, the microfluidic chip 20 may be constructed of, for example, glass or a PDMS (Polydimethylsiloxane) substance, which may also be known as dimethylpolysiloxane or dimethicone. According to some example embodiments, the microfluidic chip 20 may be constructed of polymetric organosilicon compounds or silicon-based organic compounds, which are commonly referred to as silicones. Further, according to some example embodiments, the microfluidic chip 20 may be created via an injection molding process.

The reservoir interface 40 may operate as a coupling device between the microfluidic chip 20 and the reservoirs 50. The reservoir interface 40 may operate to provide the microfluidic chip 20 and, more specifically, the microfluidic circuit 30 access to the reservoirs 50 to facilitate removal of fluids from, or delivering fluids to, the reservoirs 50. The reservoirs 50 may include a number of containment devices, such as cups, that are configured to hold a liquid. The reservoirs 50 may include one or more input reservoirs that hold input liquids for processing (e.g., for mixing). The reservoirs 50 may also include one or more output reservoirs that receive a processed liquid (e.g., a liquid mixture). The liquids that are held by the reservoirs 50 for processing may include aqueous liquids, oils, water, or the like.

As mentioned above, the microfluidic chip 20 may include a microfluidic circuit 30. According to some example embodiments, the microfluidic circuit 30 may include portions that are within the microfluidic chip 20 and portions that are external to the microfluidic chip 20 (e.g., portions that flow through the reservoirs 50). The microfluidic circuit 30 may comprise a number of interconnected channels within the microfluidic chip 20 with at least some of the channels being microfluidic channels. According to some example embodiments, some or all of the microfluidic channels of the microfluidic circuit 30 may be formed on a common plane of the microfluidic chip 20. According to some example embodiments, the channels may operate to transport fluids in the form of gases or liquids. The microfluidic channels of the microfluidic circuit 30 that transport fluids may have diameters in the tens to hundreds of microns range. The microfluidic circuit 30 may also comprise a number of ports. According to some example embodiments, a device source pressure port 22 of the microfluidic circuit 30 may be disposed on a first side of the microfluidic chip 20 to facilitate interfacing with external components of, for example, a processing control system including a vacuum or negative pressure source. According to some example embodiments, a device relief pressure port 24 of the microfluidic circuit 30 may be disposed on a second side of the microfluidic chip 20. In some example embodiments, the device relief pressure port 24 may also be configured to interface with external components of, for example, of a processing control system.

Additionally, according to some example embodiments, reservoir ports of the microfluidic chip 20, for at least some of the reservoirs 50 (e.g., input reservoirs), may be disposed on a third side of the microfluidic chip 20. According to some example embodiments, the reservoir ports may be holes in the third side of the microfluidic chip 20 that, for example, receive or interface with liquid or gas pipes of the reservoir interface. In this regard, a reservoir of reservoirs 50 may be operably coupled to a respective reservoir port, where a reservoir port comprises a liquid opening and a gas opening. According to some example embodiments, the third side of the microfluidic chip 20 may be a bottom side of the microfluidic chip 20 such that gravity maintains the fluids in the reservoirs 50 until acted upon. The first and second sides of the microfluidic chip 20 may be substantially parallel to each other, and the third side may be substantially perpendicular to both the first side and the second side. According to some example embodiments, the microfluidic channels of the microfluidic circuit 30 may be formed on a common plane through the microfluidic chip 20 with reservoir ports extending from the common plane operably coupled to the reservoir interface 40.

According to some example embodiments, the microfluidic circuit 30 may be comprised of three portions, where at least some of the portions are disposed within the microfluidic chip 20. According to some example embodiments, the microfluidic circuit 30 may comprise a source pressure gas portion 32, a liquid channel portion 34, and a relief pressure gas portion 36. With respect to the construction of the microfluidic circuit 30, the device source pressure port 22 may be operably coupled to the source pressure gas portion 32, and the source pressure gas portion 32 may be operably coupled to the liquid channel portion 34. The liquid channel portion 34 may be operably coupled to the relief pressure gas portion 36, and the relief pressure gas portion 36 may be operably coupled to the device relief pressure port 24. The source pressure gas portion 32 and the relief pressure gas portion 36 may be subjected to gas pressures. The liquid channel portion 34 may be subjected to liquid pressures.

In operation, according to some example embodiments, an initial gas pressure may be applied at the device source pressure port 22 by an external source. The applied gas pressure may be a negative pressure. In example embodiments of FIG. 1A, a negative pressure (e.g., generated by a vacuum source) is applied at the device source pressure port 22. The application of the negative gas pressure at the device source pressure port 22 may create a fluid flow 12 through the microfluidic circuit 30 traveling from the device relief pressure port 24 to the device source pressure port 22. Because the reservoirs 50 are gas-tight sealed to the reservoir interface 40, the fluid flow 12 transitions between being a gas flow and a liquid flow through the microfluidic circuit 30 and through the reservoirs 50. In this regard, due to the negative pressure applied at the device source pressure port 22, gas (e.g., air) may be pulled into the relief pressure gas portion 36 of the microfluidic circuit 30 through relief pressure port 24. It is again noted that a positive pressure source placed at an upstream position would operate in a similar manner to push gas (e.g., air) into the microfluidic circuit 30 in the same direction. Due to the fluid flow 12, the gas may be forced into the reservoirs 50, through the reservoir interface 40, that hold an input liquid as indicated by white arrow 52. The gas pressure may create a pressure differential within the reservoirs 50 with the input liquids and pressure may therefore be applied to the input liquids in the reservoirs 50, which may operate to force the input liquids into the liquid channel portion 34 of the microfluidic circuit 30, as indicated by the black arrows 53 and 54, through the reservoir interface 40. Still being subjected to the fluid flow 12, the input liquids may be mixed within the liquid channel portion 34 at a mixing junction and transported as an output liquid to an output reservoir of the reservoirs 50, as indicated by the black arrow 55, through the reservoir interface 40. Finally, gas may be forced from the output reservoir of the reservoirs 50 and into the source pressure gas portion 32, via the reservoir interface 40, as indicated by the white arrow 51, which may be pulled from the microfluidic chip 20 via the device source pressure port 22.

As such, the process of moving fluids through the microfluidic circuit 30 involves the flow of gases at the external interfaces, regardless of whether a positive pressure source is applied at an upstream position or a negative pressure is applied at a downstream position. Therefore, no liquids are transported into or out of the device source pressure port 22 or the device relief pressure port 24 during processing, in this case mixing, of the fluids. The fluid flow 12 converts between being a gas flow within the relief pressure gas portion 36, to a liquid flow in the liquid channel portion 34, to a gas flow in the source pressure gas portion 32. Because gas flows are relied upon at the ends of the processing, contamination of component external to the microfluidic device 10 and the reservoirs 50 is avoided. In this regard, the relief pressure gas portion 36 forms a first anti-contamination barrier 35 for the liquid channel portion 34 and source pressure gas portion 32 forms a second anti-contamination barrier 33 for the liquid channel portion 34 due to the gas/liquid and liquid/gas pressure transitions.

Figure 1B:
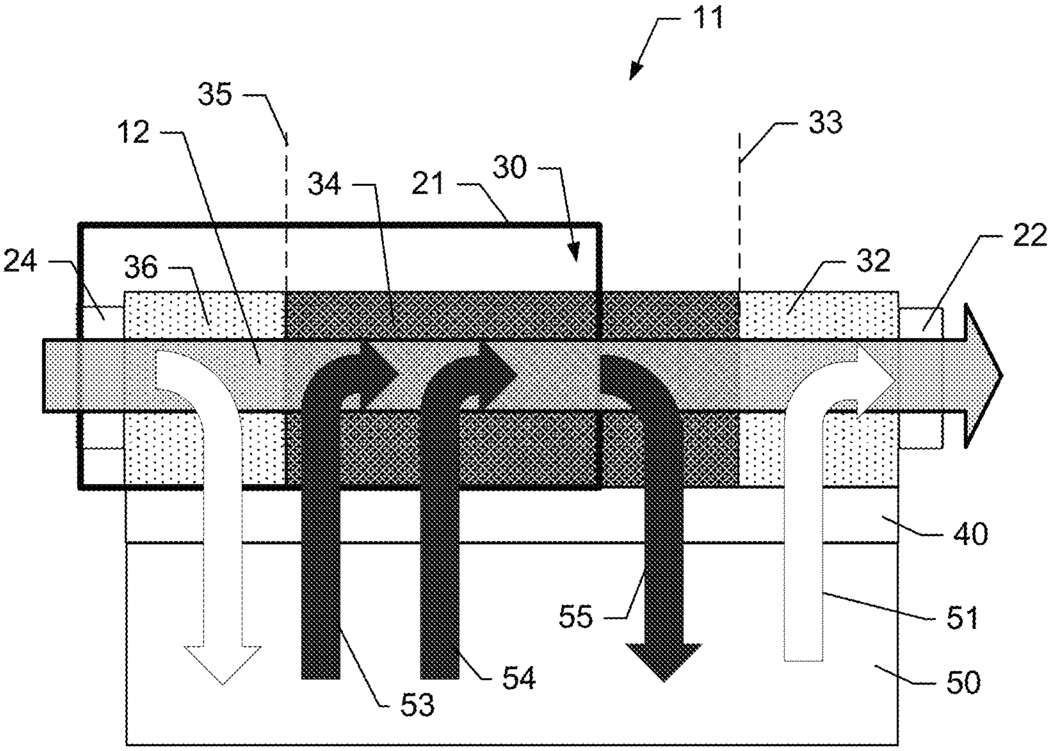
FIG. 1B illustrates another example microfluidic device and a fluid flow through the microfluidic device according to some example embodiments.

The microfluidic device 10 of FIG. 1A illustrates example embodiments where both the device source pressure port 22 and the device relief pressure port 24 are disposed on or within the microfluidic chip 20. However, according to some example embodiments, a microfluidic device may have one or both of the device source pressure port 22 or the device relief pressure port 24 disposed external to the microfluidic chip 20 as described with respect to FIG. 1B, as well as with respect to FIG. 7. The microfluidic device 11 of FIG. 1B illustrates example embodiments where, for example, the device source pressure port 22 is disposed external to the microfluidic chip 21. In this regard, for example, the output liquid may exit the microfluidic chip 21 via a tube or other conduit as shown at black arrow 55 into an output reservoir of the reservoirs 50. Despite the difference in the fluid flow 12 relative to the microfluidic chip 21, the source pressure gas portion 32 still operates to provide the second anti-contamination barrier 33 for the liquid channel portion 34 due to the gas/liquid and liquid/gas pressure transitions.

Figure 2:
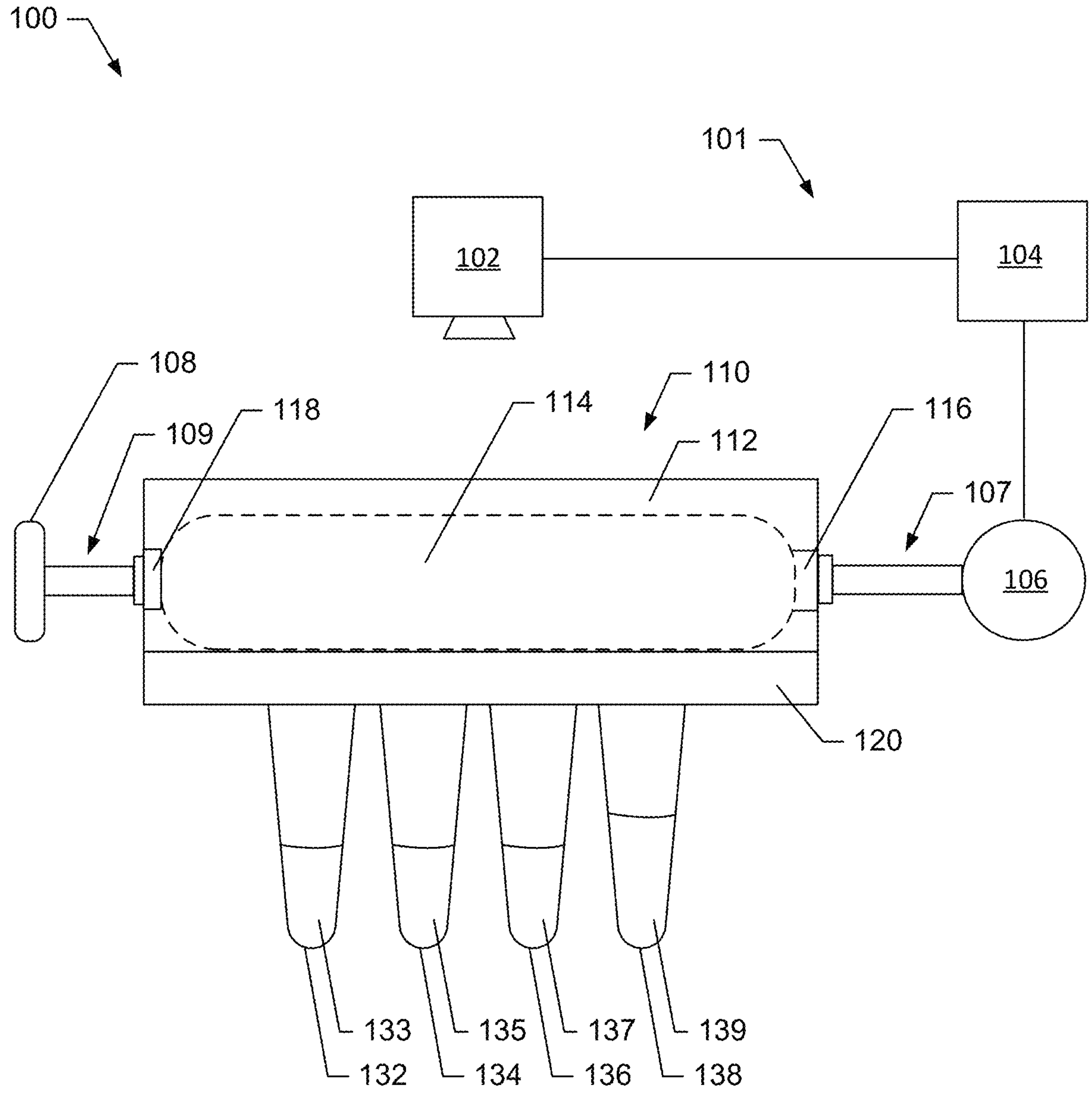
FIG. 2 illustrates an example microfluidic assembly comprising a microfluidic device and a processing control system according to some example embodiments.

Having described some of the structural and functional features of some example embodiments of a microfluidic device, reference will now be made to FIG. 2, which illustrates a microfluidic assembly 100. The microfluidic assembly 100 may comprise a microfluidic device 110 and a processing control system 101. The microfluidic device 110 may be structured and function the same or similar as the microfluidic device 10, possibly with modifications as described below and otherwise herein.

The microfluidic device 110 may comprise a microfluidic chip 112 and a reservoir interface 120. The microfluidic chip 112 may be structured and function the same or similar as the microfluidic chip 20, possibly with modifications as described below and otherwise herein. Also, the reservoir interface 120 may be structured and function the same or similar as the reservoir interface 40, possibly with modifications as described below and otherwise herein. In this regard, the reservoir interface 120 may operate as a coupling device between the microfluidic chip 112 and the reservoirs 132, 134, 136, and 138. The reservoirs 132, 134, 136, and 138 may be same or similar to reservoirs 50. Further, the reservoirs 132, 134, 136, and 138 may be, for example, formed as individual cups or canisters made of non-reactive plastic or the like. The reservoirs 132, 134, and 136 may be input reservoirs and may contain an input liquid. As such, reservoirs 132, 134, and 136 may contain input liquids 133, 135, and 137, respectively. The reservoir 138 may be an output reservoir for receiving an output liquid 139, which may be a combination of the input liquids 133, 135, and 137. Accordingly, the reservoir interface 120 may be configured to interface reservoir ports of the microfluidic circuit 114 of the microfluidic chip 112 with the internal cavity of the reservoirs 132, 134, 136, and 138 to support either removal of the liquid therein or delivery of a liquid thereto.

The microfluidic circuit 114 may be may be structured and function the same or similar as the microfluidic circuit 30, possibly with modifications as described below and otherwise herein. In this regard, the microfluidic circuit 114 may include a device source pressure port 116 and a device relief pressure port 118. With respect to functionality, the microfluidic circuit 114 may be configured to support the propagation of a fluid flow through the microfluidic circuit 114. In some example embodiments, the fluid flow may be a gas/liquid/gas flow travelling in a direction from the device relief pressure port 118 to the device source pressure port 116, where a negative pressure (e.g., vacuum) is applied at the device source pressure port 116 Alternatively, in some example embodiments, the fluid flow may be a gas/liquid/gas flow travelling in a direction from the device source pressure port 116 to the device relief pressure port 118, where a positive pressure (e.g., blower) is applied at the device source pressure port 116. Due to the fluid flow, the input fluids 133, 135, and 137 may be forced from the input reservoirs 132, 134, and 136 into channels of the microfluidic circuit 114 to be combined at a mixing junction. The mixture of liquids may exit the junction, as a result of the fluid flow, as the output fluid 139 for delivery to the output reservoir 138.

The processing control system 101 may be configured to control the processing of liquids by controlling the fluid flow through a microfluidic chip 112 of the microfluidic device 110. In this regard, the processing control system 101 may comprise a camera 102, a controller 104, and a pressure source 106. The controller 104 may be configured to communicate with and control the operation of camera 102 and the pressure source 106. In some example embodiments, the controller 104 may comprise a hardware configured processing device (e.g., an application specific integrated circuit (ASIC), field programmable logic array (FPGA)) that is specifically configured to execute the functionalities of the controller 104 described herein. According to some example embodiments, the controller 104 may comprise a software configured processor that is specially configured via the execution of software commands to execute the functionalities of the controller 104 described herein. Accordingly, the controller 104 may include a non-transitory memory device that is configured to store data and instructions for accessing by the processing device to support the execution of the functionalities described with respect to the controller 104 herein.

The camera 102 may be optical sensor or other imaging device that is configured to capture still images or video of the microfluidic chip 112, and more specifically, the microfluidic circuit 114. In this regard, because the microfluidic chip 112 may be formed of a transparent or translucent substance, and at least the fluid channels of the microfluidic circuit 114 may be disposed on a common plane within the microfluidic chip 112, images of the fluid processing may be captured by the camera 102. The captured images may be transmitted to the controller 104 for analysis.

The pressure source 106 may be any type of device that is configured to generate a positive or negative pressure, via, for example, a rotating fan. For example, if the pressure source 106 is negative pressure device, the pressure source 106 may be a vacuum device. Alternatively, if the pressure source 106 is positive pressure device, the pressure source 106 may be a blower device. According to some example embodiments, the pressure source 106 may be operably coupled to the microfluidic circuit 114 via connector 107 to the device source pressure port 116. Because the pressure source 106 does not, according to some example embodiments, come into contact with fluids during processing through the microfluidic chip 112, the pressure source 106 may be considered a non-contaminated pressure source. Alternatively, if the pressure source 106 were a positive pressure source, the pressure source 106 may be applied at 118, which may then be referred to as the device source pressure port 118.

The operation of the pressure source 106 may be controlled by the controller 104. In this regard, the controller 104 may be configured to control a pressure created by the pressure source 106 that generates a fluid flow through the microfluidic circuit 114. According to some example embodiments, the controller 104 may be configured to maintain the pressure generated by the pressure source 106 at a constant value for a controlled time period of a processing run (e.g., a mixing process). According to some example embodiments, the controller 104 may be configured to change the pressure generated by the pressure source 106 over the time period of a processing run. In this regard, the controller 104 may be configured to evaluate the image captures and associated image data provided by the camera 102 and control the pressure generated by the pressure source 106 based on the image data. In this way, the camera 102 may contribute a feedback loop for the controller 104 to control the operation of the pressure source 106.

According to some example embodiments, a filter 108 may be operably coupled to the device relief pressure port 118. The filter 108 may be a component of the microfluidic device 110 or the microfluidic assembly 101. The filter 108 may operate to capture foreign particles to avoid introducing contaminates into the microfluidic circuit 114 by the fluid flow. As such, the device relief pressure port 118 may be considered a non-contaminated filtered gas input to the microfluidic circuit 114. According to some example embodiments, the filter 108 may be operably coupled to the device relief pressure port 118 via a connection 109.

Additionally, because the fluids being processed in the microfluidic circuit 114 do not come into contact with the connections 107 and 109, the filter 108 and the pressure source 106 may be reusable between processing runs of different microfluidic devices without having to clean or replace the filter 108 or the pressure source 106. Further, the connections 107 and 109 (which may be, for example, tubing, portions of a manifold, or the like) of the processing control system 101 may also be reused in subsequent processing runs, because the connections 107 and 109 also do not come into contact with any fluids and therefore do not need to be cleaned or replaced to avoid cross-contamination.

Figure 3A:
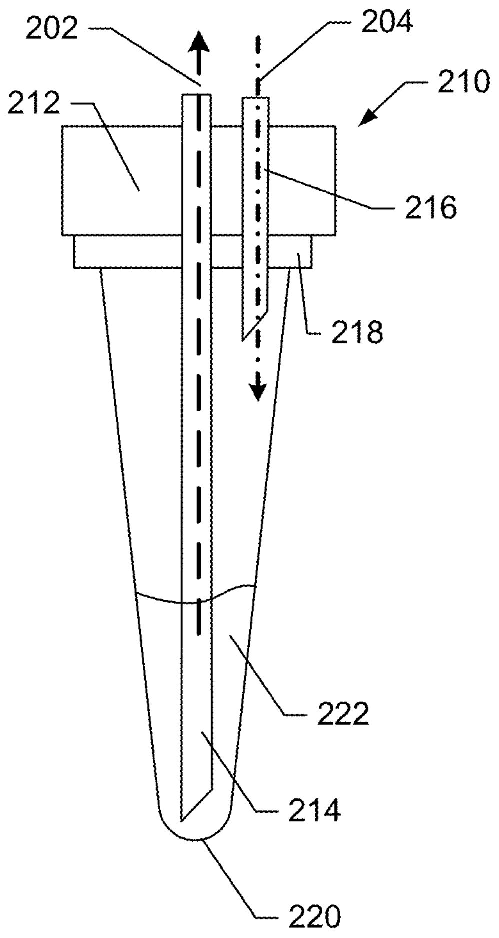
FIG. 3A illustrates an example input portion of a reservoir interface according to some example embodiments.
Figure 3B:
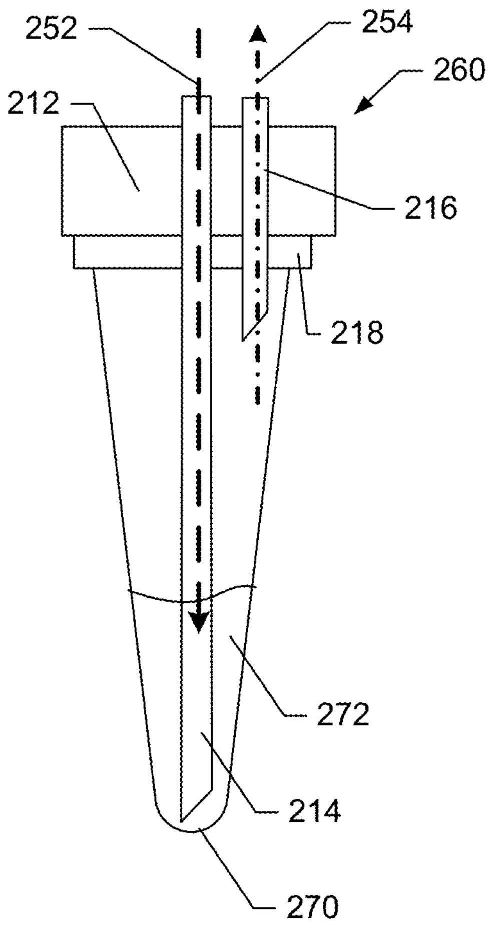
FIG. 3B illustrates the example output portion of a reservoir interface according to some example embodiments.

Now referencing FIGS. 3A and 3B, a description of portions of a reservoir interface (e.g., reservoir interface 120) with respect to an input reservoir and an output reservoir are provided. In this regard, with respect to FIG. 3A, an input reservoir interface 210 is shown. The input reservoir interface 210 may comprise a reservoir interface base 212, a liquid pipe 214, a gas pipe 216, and a gasket 218. The input reservoir interface 210 is shown as being operably coupled to an input reservoir 220 having an input liquid 222 therein.

The reservoir interface base 212 may configured to provide structural stability to the input reservoir interface 210, and the reservoir interface base 212 may be extend across a number of interfaces with respective reservoirs. The reservoir interface base 212 may therefore be a rigid structure that includes openings that align with the reservoir ports of a microfluidic circuit 114 as described herein. In this regard, the reservoir interface base 212 may include an opening for receiving and holding the liquid pipe 214 and an opening for receiving and holding a gas pipe 216. The liquid pipe 214 may be one example of a liquid interface to the reservoir 220 that is configured to transport the liquid 222 from the reservoir 220 to the liquid channel portion of the microfluidic circuit due to a liquid flow in the liquid channel portion that causes a pressure differential within the reservoir 220. As described herein, it is understood that the liquid interface to a reservoir need not include a liquid pipe, but rather any means for delivering a liquid pressure to the internal cavity of the reservoir 220. Similarly, the gas pipe 216 may be one example of a gas interface to the reservoir 220. In this regard, the gas interface may be configured to transport gas from the relief pressure gas portion into the reservoir 220 due to a gas flow in the relief pressure gas portion causing a pressure differential within the reservoir 220.

The liquid pipe 214 may be hollow tube formed of, for example, glass, plastic, etc. that extends from a liquid opening of an input reservoir port of a microfluidic circuit into the reservoir 220. As shown in FIG. 3A, according to some example embodiments, the liquid pipe 214 may extend above a top surface of the reservoir interface base 212 to facilitate alignment and insertion of the liquid pipe 214 into the liquid opening of the input reservoir port. The liquid pipe 214 may extend to the bottom or adjacent to the bottom of the reservoir 220 to ensure that the liquid pipe 214 is able to access all of the input liquid 222 that is held in the reservoir 220. According to some example embodiments, the liquid pipe 214 may have a beveled tip to facilitate retrieval of liquid at the bottom of the reservoir 220.

The gas pipe 216 may also be a hollow tube formed of, for example, glass, plastic, etc. that extends from a gas opening of an input reservoir port of a microfluidic circuit into the reservoir 220. As shown in FIG. 3A, according to some example embodiments, the gas pipe 216 may extend above a top surface of the reservoir interface base 212 to facilitate alignment and insertion of the gas pipe 216 into the gas opening of the input reservoir port of the microfluidic circuit. The gas pipe 216 may extend to a shallow depth into the reservoir 220 to limit or avoid contact with the input liquid 222.

The gasket 218 of the input reservoir interface 210 may operate to form a gas-tight seal between the internal cavity of the reservoir 220 and the input reservoir interface 210. More particularly, the seal is formed around a lip of the reservoir to ensure that the liquid interface and the gas interface are the only openings into the internal cavity of the reservoir 220 to ensure proper fluid flow through the internal cavity of the reservoir 220.

In operation, due to a negative liquid pressure, input liquid 222 may travel through the liquid pipe 214 as indicated by arrow 202. The negative liquid pressure may be associated with a fluid flow through a microfluidic circuit and may force an amount of the input liquid 222 into the liquid pipe 214 for transport through a liquid opening in an input reservoir port of the microfluidic circuit. In relation with the negative liquid pressure and the exiting of the input liquid 222, a gas flow through the gas pipe 216 indicated by arrow 204 occurs.

In some example embodiments, rather than a negative liquid pressure being applied, a positive gas pressure may be applied to the gas pipe 216 as indicated by arrow 204. The positive gas pressure may be associated with a fluid flow through a microfluidic circuit and cause an amount of the input liquid 222 to be forced (e.g., pushed) into the liquid pipe 214 for transport through a liquid opening in an input reservoir port of the microfluidic circuit. The seal formed by the gasket 218 may prevent release of gas pressure in the internal cavity to ensure proper pressure control on the input fluid 222.

Now referring to FIG. 3B, a portion of a reservoir interface in the form of an output reservoir interface 260 is shown. The output reservoir interface 260 may be structured in the same manner as input reservoir interface 210. The output reservoir interface 260 may therefore comprise a reservoir interface base 212, a liquid pipe 214, a gas pipe 216, and a gasket 218 (e.g., an output gasket) that operate in the same or similar manner, however, with respect to the output reservoir 270 that receives the output liquid 272. In this context, the liquid pipe 214 may be operably coupled to the liquid channel portion of a microfluidic circuit and the output gas interface (e.g., the gas pipe 216) may be connected to a source pressure gas portion of a microfluidic circuit.

In operation, a negative gas pressure may be applied to the gas pipe 216 as indicated by arrow 254. The negative gas pressure may be associated with a fluid flow through a microfluidic circuit and may pull an amount of gas out of the internal cavity of the reservoir 270. This negative gas pressure within the internal cavity (maintained by the seal formed by the gasket 218) may cause a negative liquid pressure in the liquid pipe 214 to pull an amount of output liquid 272 from the liquid opening of the output reservoir port of the microfluidic circuit and into the reservoir 270 as indicated by the arrow 252.

Alternatively, in some example embodiments, a positive liquid pressure may be applied to the liquid pipe 214 as indicated by arrow 252. The positive liquid pressure may be associated with a fluid flow through a microfluidic circuit and cause an amount of the output liquid 272 to be pushed into the liquid pipe 214 from a liquid opening in an output reservoir port of a microfluidic circuit. To relieve the pressure in the internal cavity, a gas flow through the gas pipe 216 indicated by arrow 254 occurs.

As such, the liquid pipe 214 may be configured to transport the output liquid 272 into the reservoir 270 from a liquid channel portion in a microfluidic circuit due to a liquid flow in the liquid channel portion causing a pressure differential within the reservoir 270. The output gas interface, in the form of the gas pipe 216, may therefore be configured to transport gas from the source pressure gas portion into the reservoir 270 due to the gas flow in the source pressure gas portion causing the pressure differential within the reservoir 270. Further, the gasket 218 may be configured to form a gas-tight seal between an internal space of the reservoir 270, a liquid channel portion of a microfluidic circuit, and a source pressure gas portion of a microfluidic circuit.

Figure 4:
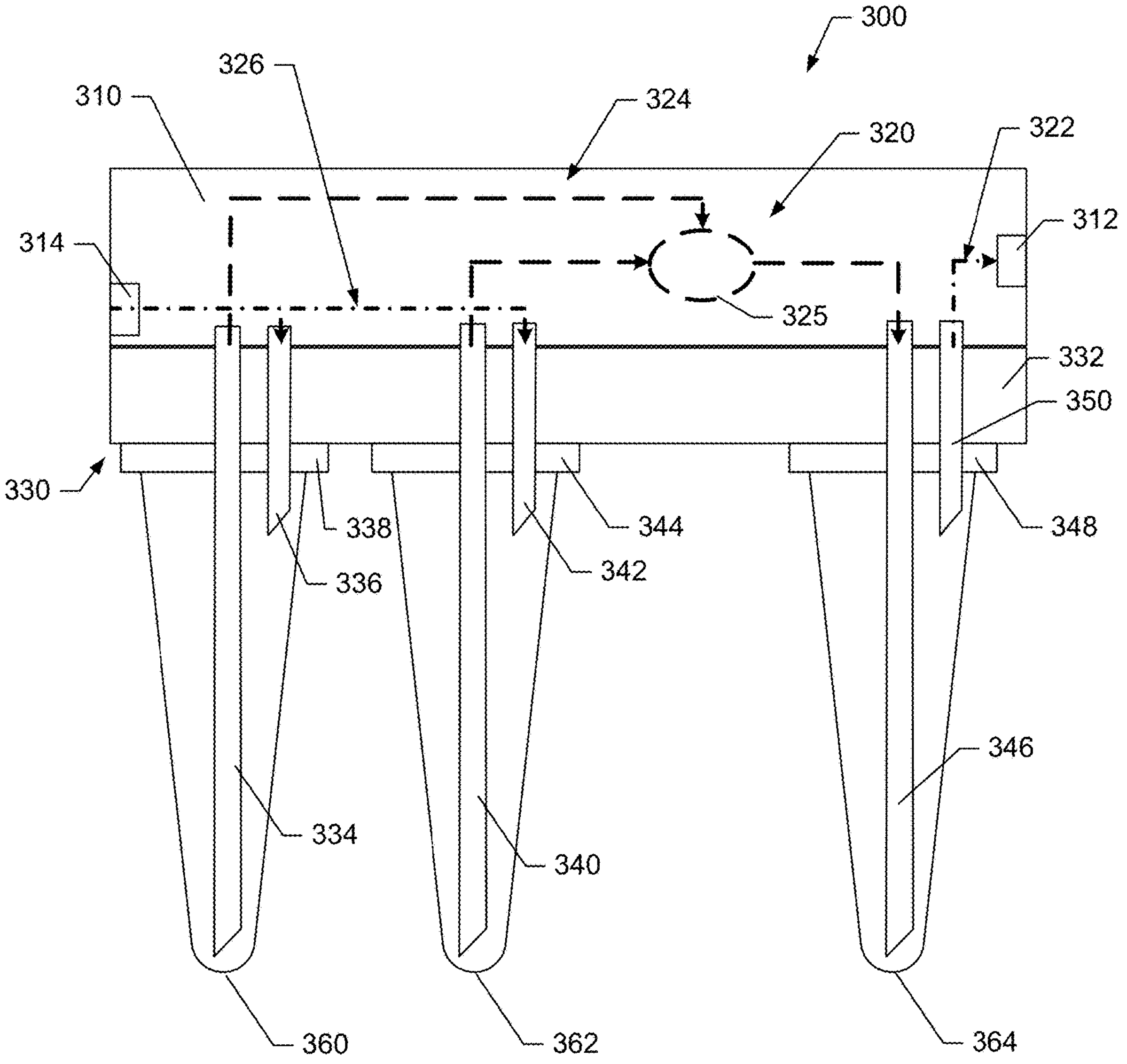
FIG. 4 illustrates an example system microfluidic device having a microfluidic circuit according to some example embodiments.

Reference will now be made to FIG. 4 to describe a microfluidic device 300 that may be a component of a microfluidic assembly. Additionally, an example architecture of a microfluidic circuit 320 of the microfluidic device 300 is provided that extends between a device source pressure port 312 and a device relief pressure port 314. The microfluidic device 300 may be constructed and function in the same or similar manner as the microfluidic device 10, the microfluidic device 110, and as otherwise described herein. Similarly, the microfluidic device 300 may comprise a microfluidic chip 310 and a reservoir interface 330. As described herein, the reservoir interface 330 may be configured to be a coupling device between the reservoirs 360, 362, and 364, and the microfluidic circuit 320.

The reservoir interface 330 may comprise a reservoir interface base 332 that secures liquid pipes 334, 340, and 346, and gas pipes 336, 342, and 350. The liquid pipes 334, 340, and 346, and the gas pipes 336, 342, and 350 may extend from openings in the microfluidic chip 310 leading to the microfluidic circuit 320 into the internal cavity of a respective reservoirs 360, 362, and 364. The reservoirs 360, 362, and 364 may, according to some example embodiments, be gas-tight sealed to the reservoir interface base 332 via respective gaskets 338, 344, and 348.

The microfluidic circuit 320 of the microfluidic chip 310 may be configured to mix two input liquids from the reservoirs 360 and 362 to form an output liquid to be delivered into reservoir 364. The microfluidic circuit 320 may comprise a number of channels that support a fluid flow in the form of a gas flow or a liquid flow through the microfluidic chip 310. The microfluidic circuit 320 may comprise ports to external components and devices. In this regard, the microfluidic circuit 320 may include a device source pressure port 312 and a device relief pressure port 314. The microfluidic circuit 320 may be formed to support a fluid flow between the device source pressure port 312 and the device relief pressure port 314.

According to some example embodiments, the microfluidic circuit 320 may comprise three portions, namely, a source pressure gas portion 322, a liquid channel portion 324, and a relief pressure gas portion 326. As described herein, the source pressure gas portion 322 and the relief pressure gas portion 326 may support gas flows, while the liquid channel portion 324 may support a liquid flow. As can be seen in FIG. 4, which provides a conceptual diagram of the microfluidic circuit 320, the source pressure gas portion 322 may comprise a channel operably coupled between the gas pipe 350 and the device source pressure port 312. Similarly, the relief pressure gas portion 326 may comprise one or more channels that connect between each gas pipe 336 and 342, and the device relief pressure port 314. Finally, the liquid channel portion 324 may comprise a number of channels that lead from the liquid pipes 334 and 340 to a mixing junction 325. The mixing junction 325 may be an intersection of some or all of the channels of the liquid channel portion 324 to perform a mixing operation at the mixing junction 325. The mixing junction 325 may have one or more output channels that lead to liquid pipes, such as liquid pipe 346.

According to some example embodiments, at least some of the channels of the liquid channel portion may have different lengths (i.e., distances from a respective reservoir port to the mixing junction 325). The length of a channel within the liquid channel portion may be considered in the design of the microfluidic chip 310, since the length of the channel may have an impact on an amount of liquid delivered to the mixing junction 325. According to some example embodiments, the length of one or more of the channels may be determined as a design parameter based on a desired liquid flow rate for a given applied pressure. In this regard, according to some example embodiments, a channel may be designed to be longer or shorter depending the desired liquid flow rate at a given pressure. Additionally or alternatively, a cross-sectional area or perimeter of a channel may also be a design parameter for obtaining a desired liquid flow rate at a given pressure.

As can be seen from the arrows indicated by the channels of the microfluidic circuit 320, as fluid flow through the microfluidic circuit 320 may be generated. As described herein, a source pressure to generate a fluid flow between the device source pressure port 312 and the device relief pressure port 314 may be applied to, for example, the device source pressure port 312. According to some example embodiments, a negative pressure may be generated at the device source pressure port 312. In doing so, a gas flow may be formed through the channel of the source pressure gas portion 322. This gas flow may create a negative pressure in the internal cavity of the reservoir 364 (i.e., the output reservoir), which may cause a liquid pressure in liquid pipe 346 (e.g., once the microfluidic circuit 320 is primed). In this regard, the microfluidic circuit 320 may be initially filled only with, for example, air. In order to arrive at a steady fluid flow, pressure may be applied to begin the flow of liquid within the microfluidic circuit 320. The microfluidic circuit 320 may be ready for steady operation or primed when the output liquid begins to fill the reservoir 364.

Additionally, the liquid pressure in liquid pipe 346 may pull liquids through the liquid pipes 334 and 340, into the microfluidic circuit 320 and into the mixing junction 325. As such, the fluid flow may cause a mixing of a first liquid in the input reservoir 360 with a second liquid in the input reservoir 362 at a mixing junction 325 of the microfluidic circuit 320 within the microfluidic chip 310 to form an output liquid. Because the liquids are being pulled from the otherwise sealed reservoirs 360 and 362, a negative gas pressure may be formed in the internal cavities of the reservoirs 360 and 362, which may be relieved by the entry of gas through the gas pipes 336 and 342 due to a gas flow from the device relief pressure port 314 through the relief pressure gas portion 326. The output liquid may therefore be delivered to the output reservoir 364 via the fluid flow through the microfluidic circuit 320. Additionally, the first liquid from the first input reservoir 360, the second liquid from the second input reservoir 362, and the output liquid delivered to the output reservoir 364 do not contact the device source pressure port 312 or the device relief pressure port 314 during the mixing.

Figure 5:
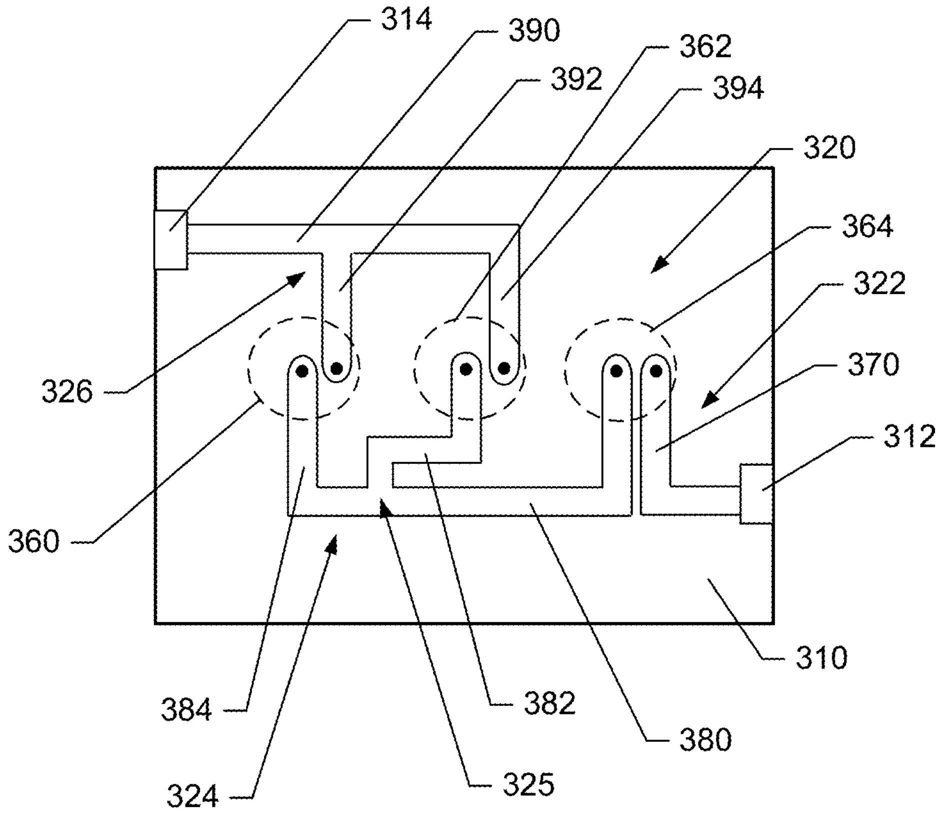
FIG. 5 illustrates an example a top view of the microfluidic device of FIG. 4 and the microfluidic circuit according to some example embodiments.

Now referring to FIG. 5, top view of an example embodiment of the microfluidic circuit 320 is shown. As mentioned herein, the microfluidic chip 310 may be formed of a transparent or translucent substance, and the channels of the microfluidic circuit 320 may be disposed on a common plane within the microfluidic chip 310. Accordingly, as provided by the top view of the microfluidic chip 310, the channels of the microfluidic circuit 320 and the contents of the channels can be visible, and can therefore be imaged, for example, by a camera (e.g., camera 102).

Following from the description of the microfluidic circuit 320 as shown in FIG. 4, the microfluidic circuit 320 as now shown in FIG. 5 includes the device source pressure port 312 operably coupled to the source pressure gas portion 322. The source pressure gas portion 322 may be operably coupled, through the reservoir 364, to the liquid channel portion 324. The liquid channel portion 324 may be operably coupled, in parallel through the reservoirs 360 and 362, to the relief pressure gas portion 326. In turn, the relief pressure gas portion 326 may be operably coupled to the device relief pressure port 314.

In this regard, a gas channel 370 may extend from the device source pressure port 312 to the gas pipe 350. Similarly, gas channels 392 and 394 may extend from gas pipes 336 and 342, respective to a common gas channel 390 that is operably coupled to the device relief pressure port 314. According to some example embodiments, the gas channels associated with the input reservoirs (e.g., reservoirs 360 and 362) may be separate channels that do not meet and connect to the device relief pressure port 314. Rather, the gas channels associated with the input reservoir extend to separate relief pressure ports that may be disposed elsewhere (e.g., on another side surface or even the top surface of the microfluidic circuit 320), but still provide a relief function to support a fluid flow through the microfluidic circuit 320. According to some example embodiments, the input reservoirs need not have gas-tight seals to allow for relief venting, and, as such, the gaskets 338 and 344 may be omitted or replaced with structure that includes relief vent holes.

With respect to the liquid channel portion 324, the liquid channels may be microfluidic channels that operate to propagate a fluid through the microfluidic circuit 320. In the example embodiment of microfluidic circuit 320, a liquid channel 380 extends from the liquid pipe 346 to the mixing junction 325 and operates as an output channel for the mixing junction 325. Liquid channel 384 extends from liquid pipe 334 to mixing junction 325 and operates as an input channel to the mixing junction 325. Similarly, liquid channel 382 extends from liquid pipe 340 to mixing junction 325 and also operates as an input channel to the mixing junction 325.

According to some example embodiments, the liquid channels (e.g., liquid channels 380, 382, 384) within the microfluidic circuit 320 may have cross-sectional areas (or diameters for circular-shaped cross-sections), that are defined based on a desired flow rate of liquid through the liquid channels. In this regard, according to some example embodiments, the cross-sectional areas of the liquid channels may be sized based on the viscosity of the liquid that is intended to be transported by the liquid channels. Further, some liquid channels may have different cross-sectional areas from other liquid channels. The different cross-sectional areas may be utilized to create different ratios of liquids in a resultant output mixture, even when leveraging a common pressure source.

Figure 6:
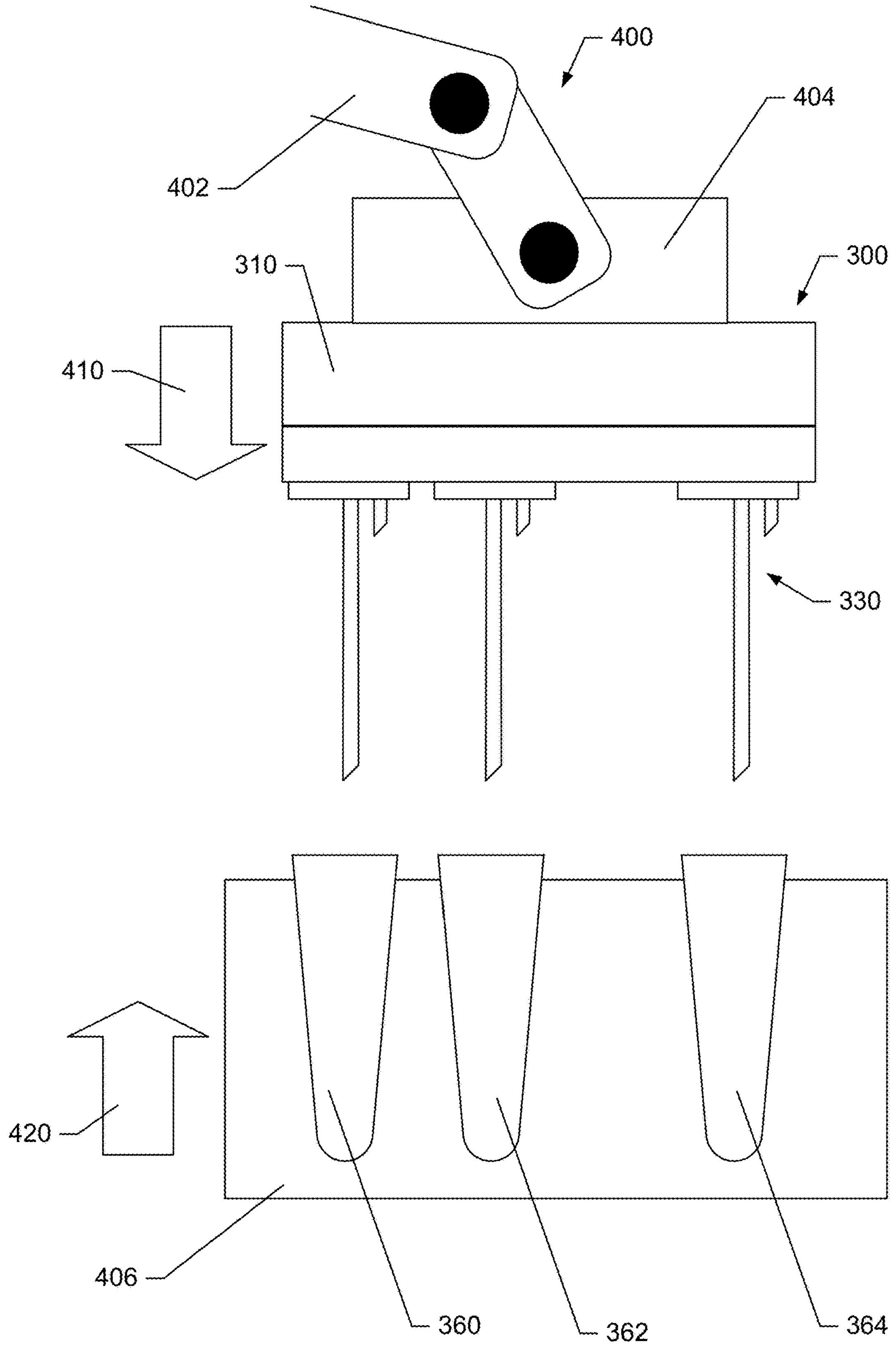
FIG. 6 illustrates a microfluidic device and reservoir tray process according to some example embodiments.

Referring now to FIG. 6, an assembly operation for the microfluidic device 300 is shown. In this regard, due to the unitary aspects of the microfluidic device 300, the microfluidic device 300 may be inserted into a tray 406 of reservoirs, such as reservoirs 360, 362, and 364. In this regard, the reservoirs 360, 362, and 364 may be affixed or secured in the tray 406 in a manner that prevents relative movement between the reservoirs 360, 362, and 364. As such, the complementary structured microfluidic device 300 may be coupled to the reservoirs 360, 362, and 364, and possibly the tray itself to form a cartridge. Such a cartridge may be configured to be installed in a processing control system (e.g., processing control system 101) as described herein. Moreover, the microfluidic chip 310, the reservoirs 360, 362, and 364, and the reservoir interface 330 may be combined to form a replaceable cartridge that is configured to be installed into and removed from a control apparatus.

According to some example embodiments, the assembly process of coupling the microfluidic device 300 to the reservoirs 360, 362, and 364, and the tray 406 may include movement of the tray 406 in a direction 420 towards the microfluidic device 300, or movement of the microfluidic device 300 in a direction 410 towards the reservoirs 360, 362, and 364, and the tray 406. According to some example embodiments, such movements may be performed by a robot, for example, comprising a robotic arm. While movement of the microfluidic device 300 or the tray may be performed by a robot, the assembly process depicted in FIG. 6 involves a robotic arm 402 of a robot 400 interfacing with the microfluidic device 300 to cause the movement. In this regard, the robotic arm 402 may comprise a temporary coupling device 404 that attaches the microfluidic device 300 to the robotic arm 402. The temporary coupling device 404 may be embodied in a number of ways, such as, a suction holding device that creates a vacuum between the device 404 and the top surface of the microfluidic chip 310 to affix the microfluidic device 300 to the robot arm 402 to support movement. As such, according to some example embodiments, the manipulation needed to assemble the microfluidic device 300 to the reservoirs 360, 362, and 364 may be minimal, which simplifies the assembly process thereby saving time and reducing potential errors. Further, the assembly to form cartridges that are prepared for processing at a later time may be performed offline in mass quantities to further streamline processing of the liquids and maximize utilization of the processing control stations. Also, because the assembled cartridges may include sealed reservoirs, spills, contamination, and cross-contamination may be prevented when handling outside of the processing control stations.

According to some example embodiments, prior to assembly as described above, the reservoirs 360, 362, and 364, disposed within the tray 406, may be accessible to deposit fluids into the reservoirs 360, 362, and 364. In this regard, a pipetting robot may interface with the open reservoirs (i.e., the input reservoirs) to add fluids prior to assembling the microfluidic device 300 with the reservoirs 360 and 362. Similarly, after mixing, a disassembly process may be undertaken to make the output reservoir 364 accessible for pipet removal of the output fluid from the output reservoir 364 (or other output reservoirs within the tray 406). The accessibility of the reservoirs in the manner may facilitate improvements in throughput, process traceability, error reduction, and reduction of cross contamination.

Figure 7:
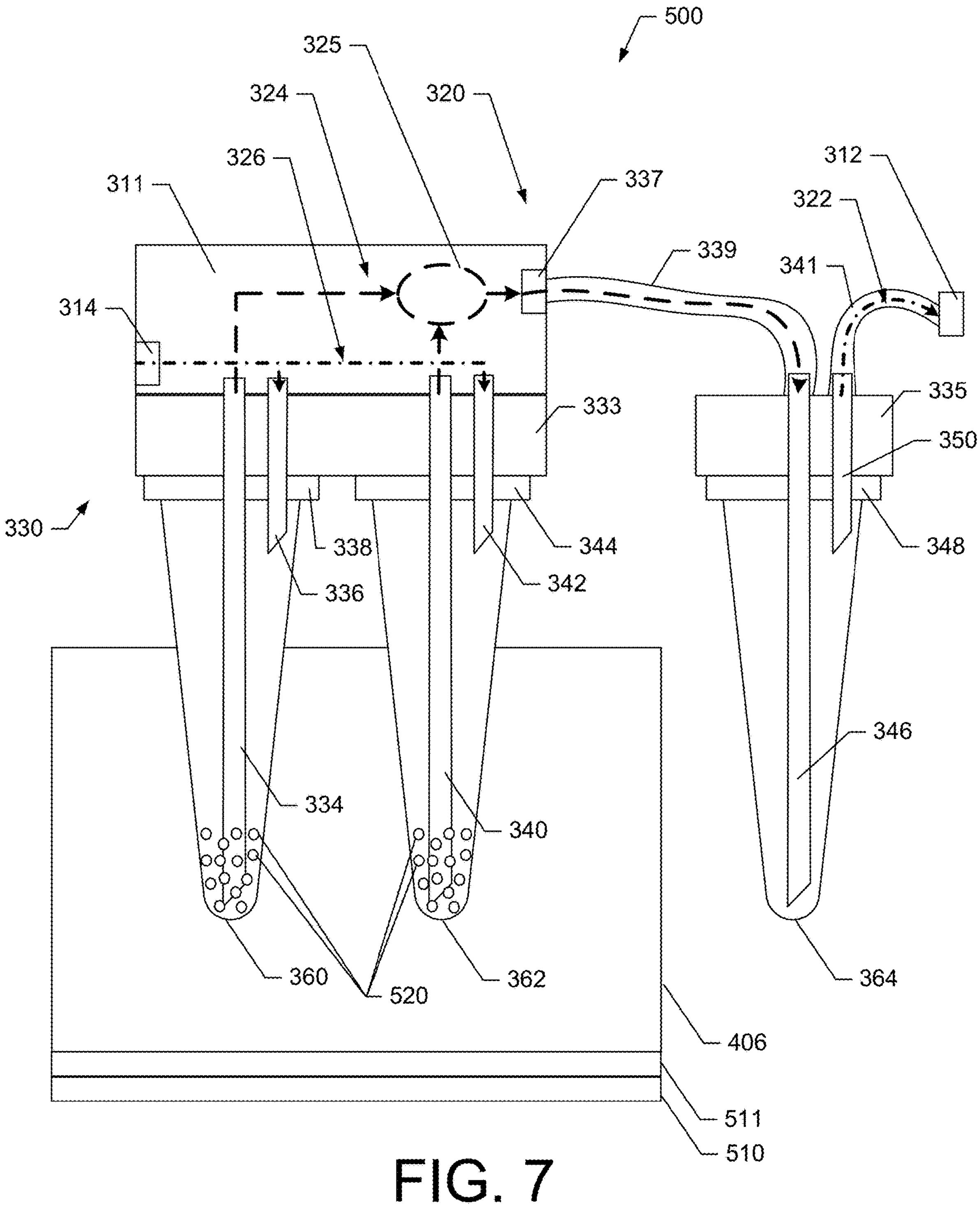
FIG. 7 illustrates another example microfluidic device having a microfluidic circuit and a separated output reservoir according to some example embodiments.

Now referring to FIG. 7, a variation of the microfluidic device 300 is provided as microfluidic device 500 where the microfluidic circuit extends beyond the microfluidic chip. In general, the microfluidic device 500 operates similar to the microfluidic device 300, but has some structural differences. In this regard, the reservoir port of the output reservoir 364 is operably coupled to the microfluidic chip 311 via tubing. In this regard, tubing 339 may be operably coupled between an output port 337 of the microfluidic chip 311 and the liquid pipe 346. The output port 337 may lead to an output of the mixing junction 325. Further, a second tube 341 may be operably coupled between the gas tube 350 and the device source pressure port 312. As such, the source pressure gas portion 322 of the microfluidic circuit 320 may be disposed within the second tube 341. Additionally, the reservoir interface 330 may have a separated reservoir interface base with a first base portion 333 supporting an interface between the input reservoirs 360 and 362 and the microfluidic chip 311, and a second base portion 335 supporting an interface between the output reservoir 364 and the tubes 339 and 322.

The input reservoirs 360 and 362 may be secured in a tray 406. In this regard, the tray 406 may operate as an interface between the reservoirs 360 and 362 and the heater 510 and/or the agitator 511. The heater 510, which may be controlled by, for example, the controller 104, may be configured to control the temperature of the input liquids within the input reservoirs 360 and 362. Additionally, the agitator 511, which may be controlled by, for example, the controller 104, may be configured to agitate the input liquids within the input reservoirs 360 and 362 via movement such as vibration. According to some example embodiments, the heater 510 and agitator 511 may be components of, for example, a heated microplate shaker.

Additionally, according to some example embodiments, micro beads 520 may be included with input liquids in the input reservoirs 360 and 362. When processing with micro beads 520 (e.g., gel beads, streptavidin beads, magnetic beads, or the like) techniques can be employed to avoid aggregation of the beads into clusters, for example, due to interactions between surfaces or molecules bound to surfaces of the input liquids (e.g., DNA). Heating (to reduce molecular bonding) via the heater 510 and agitating via the agitator 511 (to disrupt clusters and to reduce gravitational settling) may performed to improve uniformity of the distribution of the micro beads 520 during processing.

However, according to some example embodiments, heating and/or agitation of the output liquid may be not be desirable. As such, the output reservoir 364 may be mechanically separated from the input reservoirs 360 and 362 via the tubes 339 and 322 of the microfluidic device 500. For example, when the output liquid is a droplet emulsion mixed in the microfluidic chip 311, agitation may degrade the emulsion. As such, the output reservoir 364 may be mechanically separated and disposed in a non-heated and/or non-shaken mount. According to some example embodiments, flexible tubing may allow for the mechanical separation for the output reservoir 364, while maintaining the fluid flow connection to the input reservoirs 360 and 362. The input reservoirs 360 and 362 may be disposed in a heated and/or agitated mount. For example, the input reservoirs 360 and 362 may be disposed in a heated microplate shaker.

Figure 8:
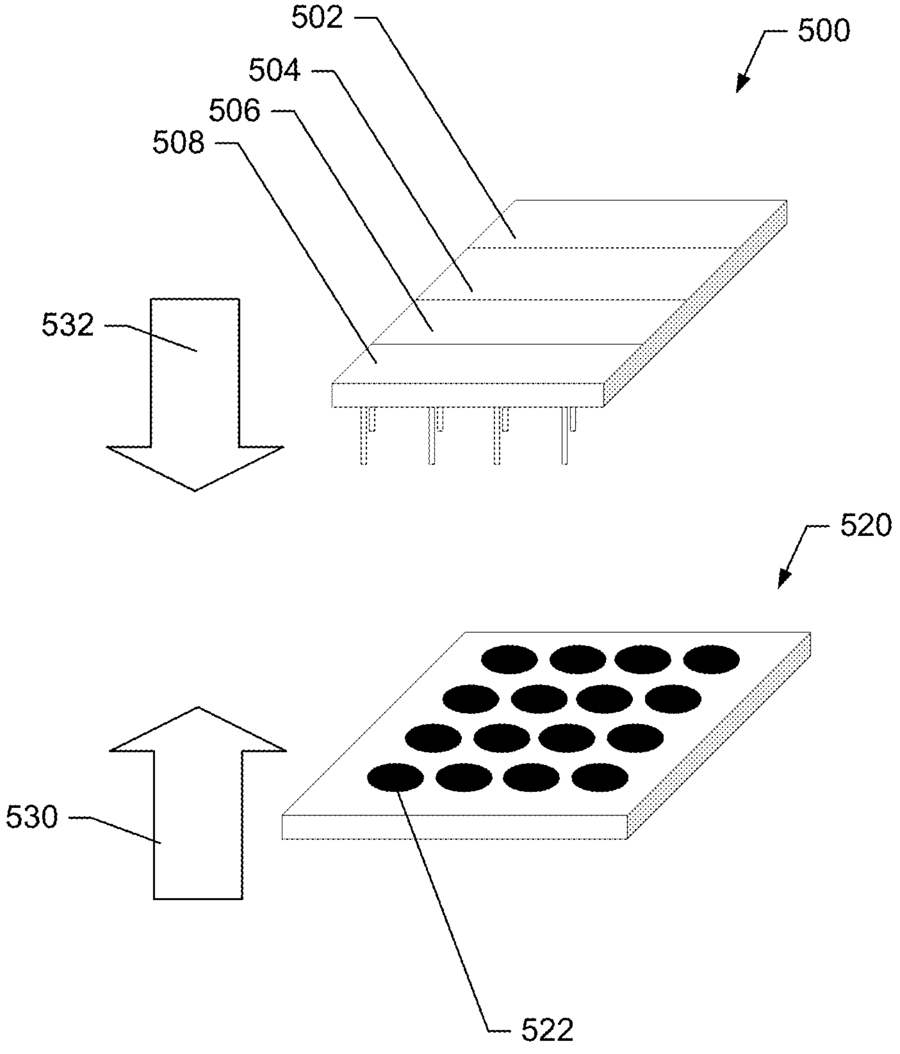
FIG. 8 illustrates a microfluidic device with an array of individual reservoir interfaces involved in a reservoir tray process according to some example embodiments.

As shown in FIG. 8, an assembly process, according to some example embodiments, may involve a microfluidic device 500 that comprises a number of subunits forming an array of individual reservoir interfaces. In this regard, for example, the microfluidic device 500 may comprise subunits 502, 504, 506, and 508 which may have respective microfluidic circuits or a common microfluidic circuit. Again, the microfluidic device 500 may be configured to interface with a tray 520 having an array of reservoirs including the reservoir 522. The assembly process may be conducted by an individual or a robot to move the microfluidic device 500 towards the tray 520 in the direction 532 or the tray 520 toward the microfluidic device 500 in the direction 530.

Figure 9:
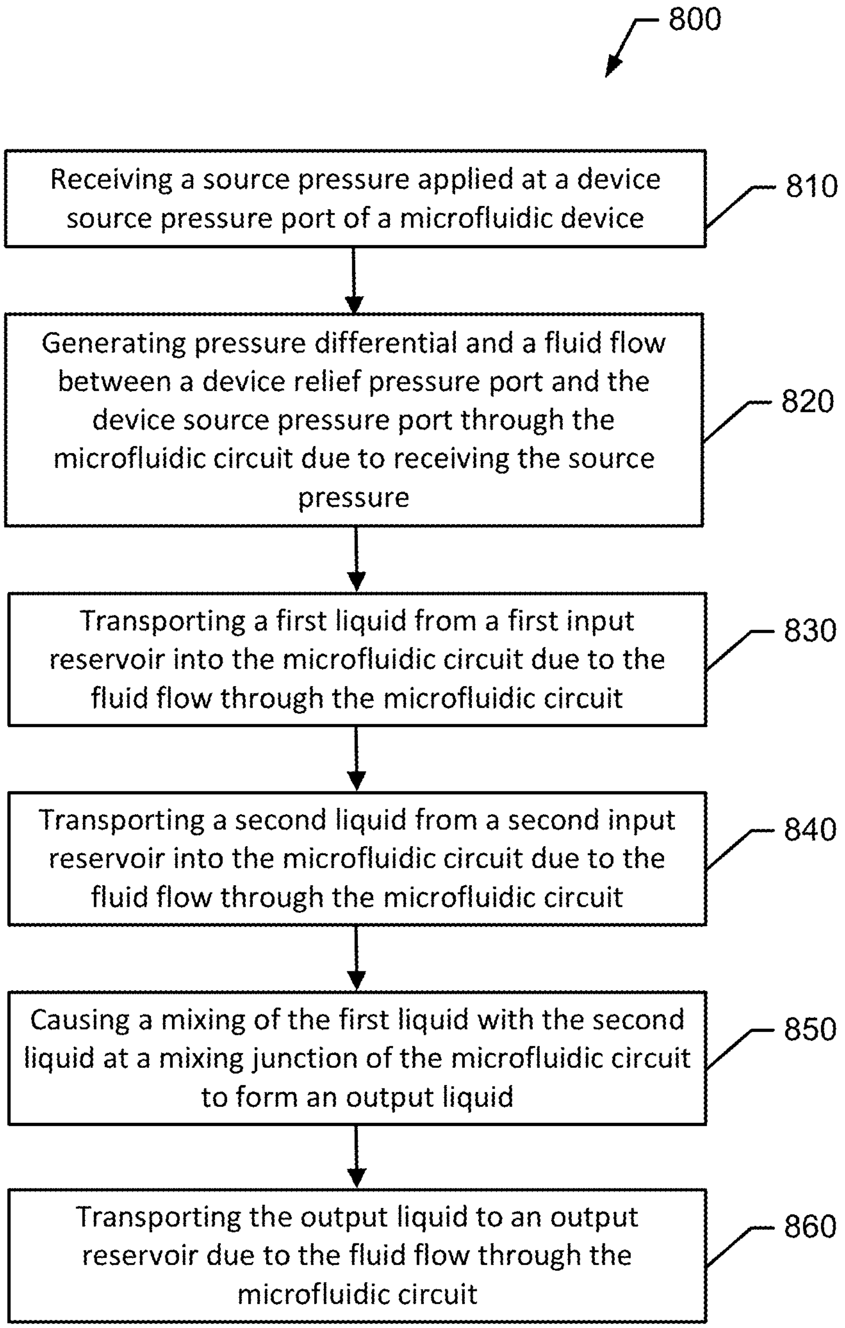
FIG. 9 illustrates a flowchart of an example method for operating a microfluidic assembly according to some example embodiments.

Now referencing FIG. 9, an example method of operating a microfluidic assembly, such as those described above, is provided. In this regard, according to some example embodiments, the example method 800 may comprise, at 810, receiving a source pressure applied at a device source pressure port of a microfluidic device, and, at 820, generating a pressure differential and a fluid flow between a device relief pressure port and the device source pressure port through the microfluidic circuit due to receiving the source pressure. The example method may further comprise, at 830, transporting a first liquid from a first input reservoir into the microfluidic circuit due to the fluid flow through the microfluidic circuit, and, at 840, transporting a second liquid from a second input reservoir into the microfluidic circuit due to the fluid flow through the microfluidic circuit. The example method may also comprise, at 850, causing a mixing of the first liquid with the second liquid at a mixing junction of the microfluidic circuit to form an output liquid. The example method may further comprise, at 860, transporting the output liquid to an output reservoir due to the fluid flow through the microfluidic circuit. In this regard, the first liquid, the second liquid, and the output liquid do not contact the device source pressure port or the device relief pressure port during the mixing or transporting.

Additionally, according to some example embodiments, generating the fluid flow between the device relief pressure port and the device source pressure port may comprise generating a source gas flow through a source pressure gas portion of the microfluidic device that is operably coupled to the device source pressure port, generating a liquid flow through a liquid channel portion of the microfluidic circuit that is operably coupled to the source pressure gas portion through the output reservoir, and generating a relief gas flow through a relief pressure gas portion of the microfluidic circuit that is operably coupled to the device relief pressure port and to the liquid channel portion through the first input reservoir and the second input reservoir.

Additionally or alternatively, according to some example embodiments, generating the relief gas flow through the relief pressure gas portion may further comprise generating the relief gas flow through a filter operably coupled to the device relief pressure port. Additionally or alternatively, according to some example embodiments, transporting the first liquid may comprise transporting the first liquid through a liquid pipe that extends into the first input reservoir and into the first liquid. Additionally or alternatively, according to some example embodiments, transporting the first liquid from the first input reservoir may further comprise transporting gas into the first input reservoir via a first gas interface to the microfluidic circuit.

The embodiments present herein are provided as examples and therefore the associated inventions are not to be limited to the specific embodiments disclosed. Modifications and other embodiments are intended to be included within the scope of the appended claims. Moreover, although the foregoing descriptions and the associated drawings describe example embodiments in the context of certain example combinations of elements and/or functions, different combinations of elements and/or functions may be used to form alternative embodiments. In this regard, for example, different combinations of elements and/or functions other than those explicitly described above are also contemplated. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments.

That which is claimed:

1. A microfluidic assembly comprising:

a device source pressure port;

a device relief pressure port;

a microfluidic chip operably coupled to the device source pressure port and the device relief pressure port, the microfluidic chip comprising a microfluidic circuit configured to support a fluid flow through the microfluidic circuit, the fluid flow comprising a gas flow and a liquid flow within the microfluidic circuit;

a first input reservoir and a second input reservoir;

an output reservoir; and a reservoir interface configured to operably couple the first input reservoir and the second input reservoir to the microfluidic circuit;

wherein the device source pressure port is configured to receive a source pressure to generate a fluid flow between the device relief pressure port and the device source pressure port and through the microfluidic circuit, the fluid flow causing a mixing of a first liquid in the first input reservoir with a second liquid in the second input reservoir at a mixing junction of the microfluidic circuit within the microfluidic chip to form an output liquid for delivery to the output reservoir via the fluid flow, wherein the first liquid, the second liquid, and the output liquid do not contact the device source pressure port or the device relief pressure port during the mixing.

2. The microfluidic assembly of claim 1 comprising a source pressure gas portion, a relief pressure gas portion, and a liquid channel portion, the liquid channel portion comprising the mixing junction;

wherein the device source pressure port is operably coupled to the source pressure gas portion, the source pressure gas portion is operably coupled to the liquid channel portion, the liquid channel portion is operably coupled to the relief pressure gas portion, and the relief pressure gas portion is operably coupled to the device relief pressure port;

wherein the fluid flow through the source pressure gas portion and the relief pressure gas portion is a gas flow; and wherein the fluid flow through the liquid channel portion is a liquid flow.

3. The microfluidic assembly of claim 2, wherein the reservoir interface comprises an interface base that supports a first input reservoir interface, the first input reservoir interface comprising a first liquid pipe and a first gas interface;

wherein the first liquid pipe is operably coupled to the liquid channel portion of the microfluidic circuit and the first gas interface is operably coupled to the relief pressure gas portion;

wherein the first liquid pipe extends from the interface base into the first liquid within the first input reservoir;

wherein the first liquid pipe is configured to transport the first liquid from the first input reservoir to the liquid channel portion due to the liquid flow in the liquid channel portion causing a pressure differential within the first input reservoir;

wherein the first gas interface is configured to transport gas from the relief pressure gas portion into the first input reservoir due to the gas flow in the relief pressure gas portion causing the pressure differential within the first input reservoir.

4. The microfluidic assembly of claim 2 further comprising an output reservoir interface comprising an output liquid pipe and an output gas interface;

wherein the output liquid pipe is operably coupled to the liquid channel portion of the microfluidic circuit and the output gas interface is connected to the source pressure gas portion;

wherein the output liquid pipe is configured to transport the output liquid into the output reservoir from the liquid channel portion due to the liquid flow in the liquid channel portion causing a pressure differential within the output reservoir;

wherein the output gas interface is configured to transport gas from the source pressure gas portion into the output reservoir due to the gas flow in the source pressure gas portion causing the pressure differential within the output reservoir.

5. The microfluidic assembly of claim 4, wherein the reservoir interface comprises an output gasket configured to form a gas-tight seal between an internal space of the output reservoir, the liquid channel portion, and the source pressure gas portion.

6. The microfluidic assembly of claim 1, wherein the device source pressure port is connected to a vacuum source.

7. The microfluidic assembly of claim 1, where in the device relief pressure port is connected to a filter.

8. The microfluidic assembly of claim 1, wherein micro beads are included in the first input reservoir;

wherein the microfluidic assembly further comprises an agitator configured to agitate, or a heater configured to heat, the first liquid and the micro beads in the first input reservoir during the mixing to inhibit settling and clustering of the micro beads within the first input reservoir.

9. The microfluidic assembly of claim 1, wherein the microfluidic chip, the first input reservoir, the second input reservoir, the output reservoir, and the reservoir interface form a replaceable cartridge that is configured to be installed into and removed from a control apparatus.

10. The microfluidic assembly of claim 9, wherein the replaceable cartridge is configured to be installed and removed from the control apparatus by a robot.

11. The microfluidic assembly of claim 1 further comprising:

a vacuum source connected to the device source pressure port;

a camera configured to image the microfluidic chip; and a controller configured to receive and evaluate images of the fluid flow in the microfluidic circuit from the camera and responsively adjust a pressure provided by the vacuum source.

12. A microfluidic reservoir interface comprising:

a liquid pipe configured to extend into a liquid within a first input reservoir;

a gas interface; and an interface base configured to support the liquid pipe and the gas interface;

wherein the liquid pipe is configured to be operable coupled to a liquid channel portion of a microfluidic circuit of a microfluidic chip and the gas interface is configured to be operably coupled to a gas channel portion of a microfluidic device;

wherein the liquid pipe is configured to transport the liquid between the first input reservoir and the liquid channel portion in response to a fluid flow through the liquid pipe and the gas interface;

wherein a device source pressure port is configured to receive a source pressure to generate a fluid flow between a device relief pressure port and the device source pressure port and through the microfluidic circuit, the fluid flow causing a mixing of a first liquid in the first input reservoir with a second liquid in a second input reservoir at a mixing junction of the microfluidic circuit within the microfluidic chip to form an output liquid for delivery to an output reservoir via the fluid flow; and wherein a first liquid, a second liquid, and a output liquid do not contact the device source pressure port or the device relief pressure port during the mixing.

13. The microfluidic reservoir interface of claim 12 further comprising a gasket configured to form a gas-tight seal between an internal space of the first input reservoir, the liquid channel portion, and a source pressure gas portion of the microfluidic device to facilitate a liquid flow through the liquid pipe and a gas flow through the gas interface.

14. The microfluidic reservoir interface of claim 12 wherein the liquid pipe is operably coupled to a gas pressure source to generate a liquid flow through the liquid pipe due to the fluid flow and an associated pressure differential in the first input reservoir.

15. The microfluidic reservoir interface of claim 12 wherein the gas interface comprises a gas pipe;

wherein the liquid pipe extends deeper into the first input reservoir than the gas pipe such that the liquid pipe extends below a surface of the liquid within the first input reservoir and the gas pipe remains above the surface of the liquid within the first input reservoir.

16. A method comprising:

receiving a source pressure applied at a device source pressure port of a microfluidic device;

generating a pressure differential and a fluid flow between a device relief pressure port and the device source pressure port through a microfluidic circuit due to receiving the source pressure;

transporting a first liquid from a first input reservoir into the microfluidic circuit due to the fluid flow through the microfluidic circuit;

transporting a second liquid from a second input reservoir into the microfluidic circuit due to the fluid flow through the microfluidic circuit;

causing a mixing of the first liquid with the second liquid at a mixing junction of the microfluidic circuit to form an output liquid; and transporting the output liquid to an output reservoir due to the fluid flow through the microfluidic circuit;

wherein the first liquid, the second liquid, and the output liquid do not contact the device source pressure port or the device relief pressure port during the mixing.

17. The method of claim 16, wherein generating the fluid flow between the device relief pressure port and the device source pressure port comprises:

generating a source gas flow through a source pressure gas portion of the microfluidic device that is operably coupled to the device source pressure port;

generating a liquid flow through a liquid channel portion of the microfluidic circuit that is operably coupled to the source pressure gas portion through the output reservoir; and generating a relief gas flow through a relief pressure gas portion of the microfluidic circuit that is connected to the device relief pressure port and to the liquid channel portion through the first input reservoir and the second input reservoir.

18. The method of claim 17 wherein generating the relief gas flow through the relief pressure gas portion further comprises generating the relief gas flow through a filter connected to the device relief pressure port.

19. The method of claim 16 wherein transporting the first liquid comprises transporting the first liquid through a liquid pipe that extends into the first input reservoir and into the first liquid.

20. The method of claim 16 wherein transporting the first liquid from the first input reservoir further comprises transporting gas into the first input reservoir via a first gas interface to the microfluidic circuit.

* * * * *